United States Patent
Shelley, Jr. et al.

(10) Patent No.: US 9,606,070 B2
(45) Date of Patent: Mar. 28, 2017

(54) MULTISPECTRAL IMAGING SYSTEM AND METHOD FOR DETECTING FOREIGN OBJECT DEBRIS

(71) Applicant: The Boeing Company, Chicago, IL (US)

(72) Inventors: Paul H Shelley, Jr., Lakewood, WA (US); Paul G Vahey, Seattle, WA (US); Gregory J Werner, Lacey, WA (US); Robert Arthur Kisch, Auburn, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 14/552,697

(22) Filed: Nov. 25, 2014

(65) Prior Publication Data

US 2016/0146741 A1 May 26, 2016

(51) Int. Cl.
*G01N 21/94* (2006.01)
*G01N 21/88* (2006.01)
*B29C 70/38* (2006.01)
*G01N 21/84* (2006.01)

(52) U.S. Cl.
CPC .......... *G01N 21/94* (2013.01); *B29C 70/382* (2013.01); *G01N 21/8806* (2013.01); *G01N 2021/8472* (2013.01)

(58) Field of Classification Search
CPC ........ G01N 21/00; G01N 21/35; G01N 21/94; G01N 21/8806; G01J 5/02
See application file for complete search history.

(56) References Cited

U.S. PATENT DOCUMENTS

| | | |
|---|---|---|
| 8,338,787 B1 | 12/2012 | Shelley et al. |
| 8,853,634 B2 | 10/2014 | Shelley, Jr. et al. |
| 2007/0097359 A1 | 5/2007 | Engelbart et al. |
| 2008/0289742 A1 | 11/2008 | Engelbart et al. |
| 2013/0234030 A1 | 9/2013 | Shelley, Jr. et al. |

OTHER PUBLICATIONS

Avdelidis et al, "The technology of composite patches and their structural reliability inspection using infrared imaging", 2003, Progress in Aerospace Sciences 39 (2003) 317-328.*

* cited by examiner

*Primary Examiner* — David Porta
*Assistant Examiner* — Faye Boosalis
(74) *Attorney, Agent, or Firm* — Alston & Bird LLP

(57) ABSTRACT

A multispectral imaging system and method and a system for composite layup are provided in order to detect foreign object debris during the fabrication of a composite structure. In the context of a method, a surface of a composite material is illuminated with near infrared light. The method also detects the near infrared light following interaction of the near infrared light with the composite material. Following detection, the method analyzes a spectrum of the near infrared light to detect foreign object debris upon the composite material. The method analyzes the spectrum of near infrared light by distinguishing between different types of foreign object debris as a result of comparing the spectrum of near infrared light to predefined spectral signatures of a plurality of different types of foreign object debris. The method may also determine the size and location of the foreign object debris.

19 Claims, 6 Drawing Sheets

MULTISPECTRAL IMAGING SYSTEM AND METHOD FOR DETECTING FOREIGN OBJECT DEBRIS

TECHNOLOGICAL FIELD

The system and method of an example embodiment relates generally to the detection of foreign object debris and, more particularly, to the detection of foreign object debris with near infrared light during the layup of composite material.

BACKGROUND

A number of structures are formed of composite materials. For example, many vehicles, such as aircraft, space craft, marine vehicles or the like, include a body that is formed at least partially, if not largely, of composite materials. Regardless of the type of composite structure, a number of composite structures are formed by laying up a plurality of composite plies with each subsequent composite ply being sequentially placed upon a prior composite ply.

During the fabrication of a composite structure, a variety of foreign object debris may be introduced. For example, the foreign object debris may include water, oil or other liquids, fasteners, pieces of wire or other relatively small pieces and parts, or any other type of foreign object. The foreign object debris may come to rest upon a composite ply and, if not removed, may be covered by subsequent composite plies and incorporated into the composite structure. Foreign object debris may create a variety of issues for the resulting composite structure. For example, the foreign object debris may reduce the integrity of the resulting composite structure, may add undesired weight to the composite structure and may adversely impact various material properties, such as the strength to weight ratio, of the composite structure.

As such, the composite structure may be inspected during the fabrication process in an effort to identify and remove foreign object debris. For example, the composite plies may be visually inspected as the composite plies are laid up in order to identify and remove foreign object debris. In order to conduct a thorough visual inspection of a composite ply, however, more time may be required for the visual inspection than would be desired, as at least some of the time required for visual inspection may slow the overall fabrication process. Additionally, it may be difficult to identify, with a visual inspection, foreign object debris that is transparent as well as foreign object debris that does not present a contrast with the background, such as foreign object debris that is black on a black background. Further, performance of the visual inspection process itself may be a source of foreign object debris with the foreign object debris being contributed by the inspector of their clothing or other accessories, such as in instances in which items fall from the inspector's pockets onto the composite structure.

In some cases, it is desirable to increase the rate at which composite structures may be fabricated and/or to allow larger composite structures to be fabricated within a desired time period by increasing the speed with which composite plies are being laid up. However, as the speed with which the composite plies are laid up increases, the time allotted for inspection of the composite plies to identify foreign object debris may be reduced, thereby increasing the difficulties associated with visually inspecting composite plies in a thorough manner to identify foreign object debris during the fabrication of the composite structure. In this regard, the time required for visual inspection may serve as a limiting factor for the speed with which a composite structure is fabricated in some instances.

BRIEF SUMMARY

A multispectral imaging system and method and a system for composite layup are provided in accordance with example embodiments of the present invention in order to detect foreign object debris in an efficient manner during the fabrication of a composite structure. In this regard, the multispectral imaging system and method utilize near infrared light to permit different types of foreign object debris to be reliably identified in a timely manner. As such, the multispectral imaging system and method and the associated system for composite layup may identify and, if desired, allow for removal of foreign object debris during the fabrication of the composite structure without impeding the layup of the composite material, even as the speed with which the composite material is laid up is increased. As such, the multispectral imaging system and method and the associated system for composite layup permit composite structures to be fabricated in an efficient and timely manner while continuing to police the composite structure for foreign object debris during the layup of the composite materials that form the composite structure.

In an example embodiment, a method is provided that includes illuminating a surface of a composite material with near infrared light. The method of this example embodiment also detects the near infrared light following interaction of the near infrared light with the composite material. Following detection, the method of this example embodiment analyzes a spectrum of the near infrared light to detect foreign object debris upon the composite material. In this regard, the method analyzes the spectrum of near infrared light by distinguishing between different types of foreign object debris as a result of comparing the spectrum of near infrared light to predefined spectral signatures of a plurality of different types of foreign object debris. In an example embodiment, the steps of illuminating, detecting and analyzing are performed simultaneous with the layup of the composite material.

The method of an example embodiment detects the near infrared light by separately capturing the spectrum of near infrared light with each of a plurality of detector elements following the interaction of the near infrared light with a respective portion of the composite material. Each detector element corresponds to a respective pixel. The method of this example embodiment may also include identifying foreign object debris of a respective type upon the composite material in an instance in which at least a predetermined number of adjacent pixels have a spectrum of near infrared light that corresponds to the predefined spectral signature of the respective type of foreign object debris. The method of an example embodiment illuminates the surface of the composite material with light having a wavelength within only a portion of the near infrared spectrum. For example, the surface of the composite material may be illuminated with light having wavelengths between 900 nanometers and 2500 nanometers and, more particularly, between 900 nanometers and 1700 nanometers.

In another example embodiment, a multispectral imaging system is provided that includes a near infrared light source configured to illuminate a surface of a composite material with near infrared light. The multispectral imaging system of this example embodiment also includes a detector configured to detect the near infrared light following interaction of the near infrared light with the composite material. The multispectral imaging system of this example embodiment further includes processing circuitry, responsive to the detector, configured to analyze a spectrum of the near infrared light to detect foreign object debris upon the composite material. The processing circuitry is configured to analyze the spectrum of near infrared light by distinguishing between different types of foreign object debris as a result of comparing the spectrum of near infrared light to predefined spectral signatures of the plurality of different types of foreign object debris.

A detector of an example embodiment includes a plurality of detector elements that are each configured to separately capture the spectrum of near infrared light following the interaction of the near infrared light with a respective portion of the composite material. Each detector element corresponds to a respective pixel. The processing circuitry of this example embodiment may be further configured to identify foreign object debris of a respective type upon the composite material in an instance in which at least a predetermined number of adjacent pixels have a spectrum of near infrared light that corresponds to the predefined spectral signature of the respective type of foreign object debris. The near infrared light source of an example embodiment is configured to illuminate the surface of the composite material with light having a wavelength within only a portion of the near infrared spectrum. For example, the near infrared light source may be configured to illuminate the surface of the composite material with light having wavelengths between 900 nanometers and 2500 nanometers and, more particularly, with light having wavelengths between 900 nanometers and 1700 nanometers.

In a further example embodiment, a system for composite layup is provided that includes an automatic fiber placement apparatus configured to apply composite material to a workpiece. The automatic fiber placement apparatus is configured to move relative to the workpiece. The system of this example embodiment also includes a multispectral imaging system that includes a near infrared light source configured to illuminate a surface of the composite material with near infrared light. The multispectral imaging system also includes a detector configured to detect the near infrared light following interaction of the near infrared light with the composite material. The multispectral imaging system further includes processing circuitry, responsive to the detector, configured to analyze a spectrum of the near infrared light to detect foreign object debris upon the composite material while the composite material is applied to the workpiece. The near infrared light source and the detector are configured to move with the automatic fiber placement apparatus relative to the workpiece while the composite material is applied to the workpiece.

The processing circuitry of an example embodiment is further configured to analyze the spectrum of near infrared light by distinguishing between different types of foreign object debris as a result of comparing the spectrum of near infrared light to predefined spectral signatures of a plurality of different types of foreign object debris. The detector of this example embodiment may include a plurality of detector elements that are each configured to separately capture the spectrum of near infrared light following the interaction of the near infrared light with a respective portion of the composite material. Each detector element corresponds to a respective pixel. The processing circuitry of this example embodiment may be further configured to identify foreign object debris of a respective type upon the composite material in an instance in which a predetermined number of adjacent pixels represent a spectrum of near infrared light that corresponds to the predefined spectral signature of the respective type of foreign object debris.

The near infrared light source of an example embodiment is configured to illuminate the surface of the composite material with light having wavelengths between 900 nanometers and 1700 nanometers. The processing circuitry of an example embodiment is further configured to associate a location with foreign object debris detected upon the composite material based upon location information provided by the automatic fiber replacement apparatus. The processing circuitry of an example embodiment is further configured to cause a notification to be provided of the foreign object debris detected upon the composite material prior to covering the foreign object debris with additional composite material applied by the automatic fiber replacement apparatus.

BRIEF DESCRIPTION OF THE DRAWINGS

Figure 1:
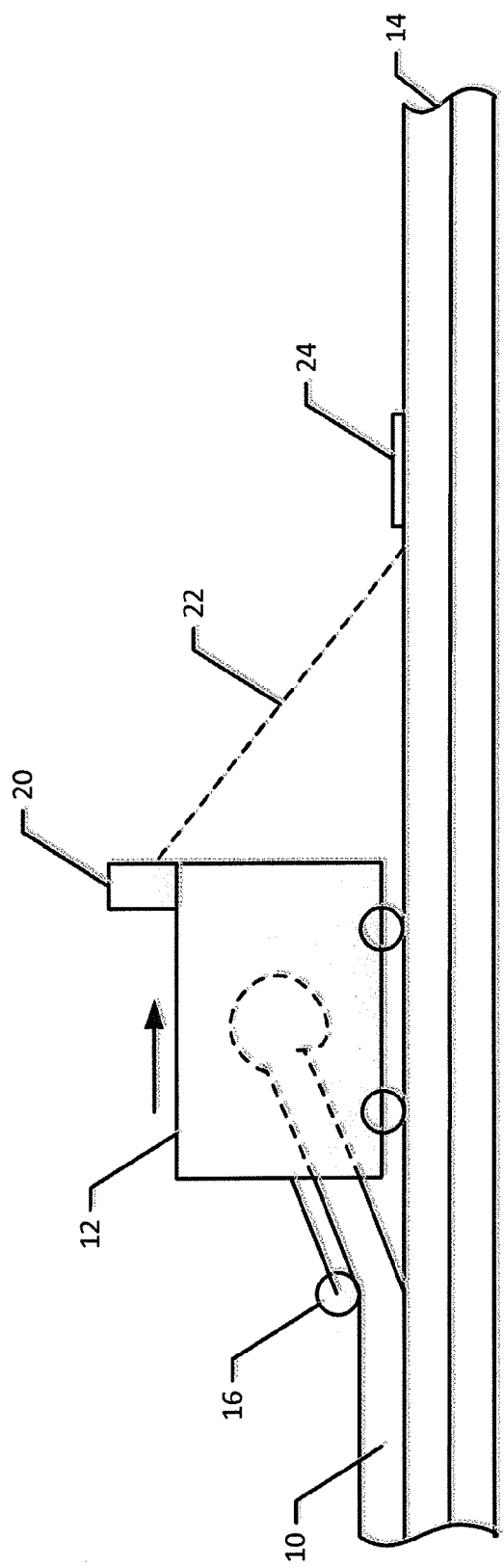
Figure 2:
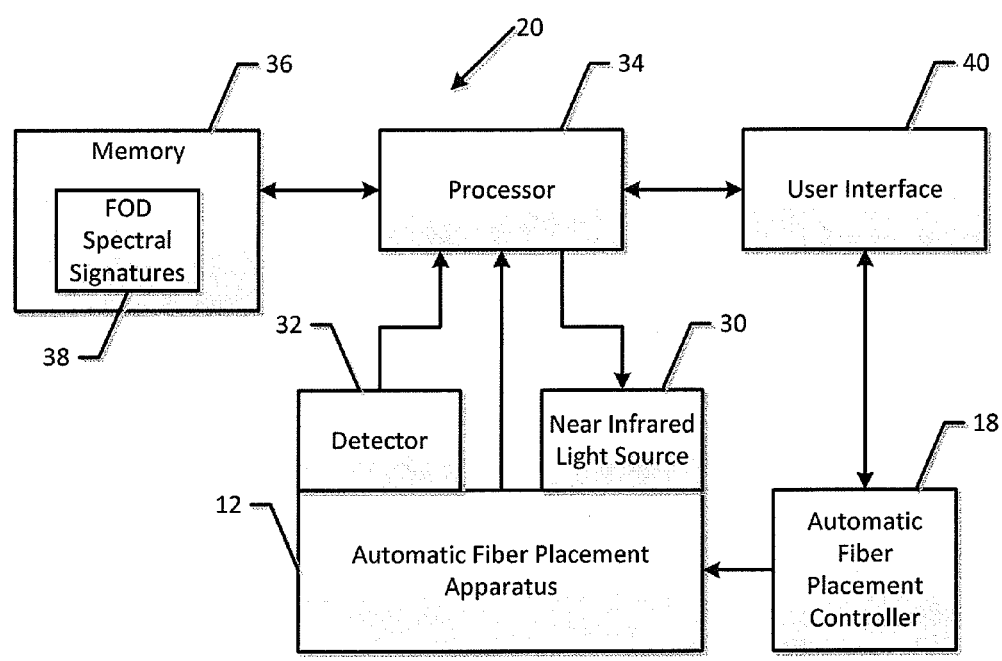
Figure 3:
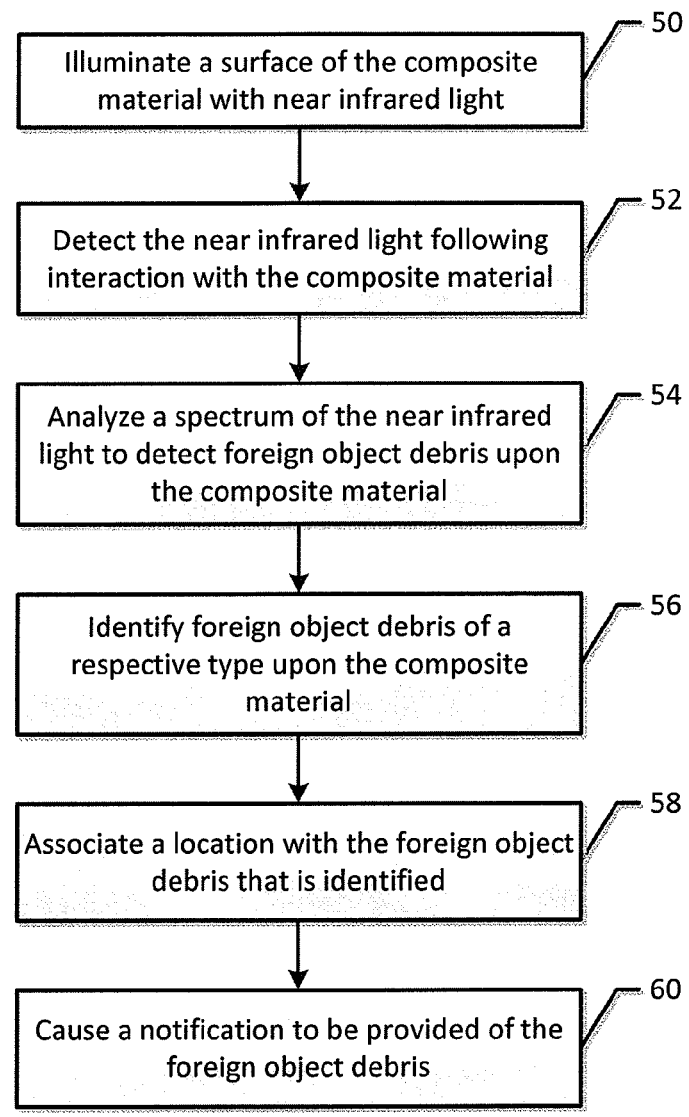
Figure 4:
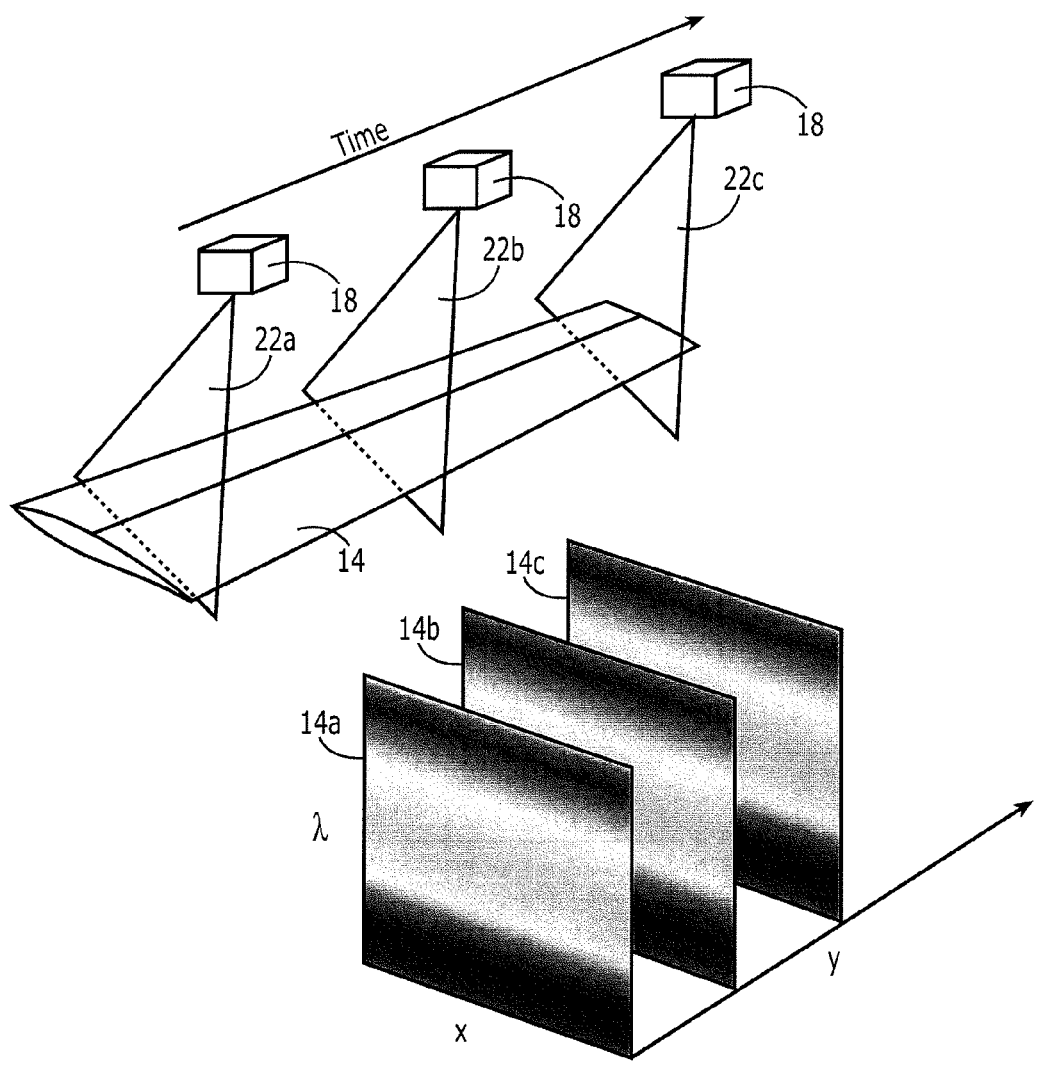
Figure 5:
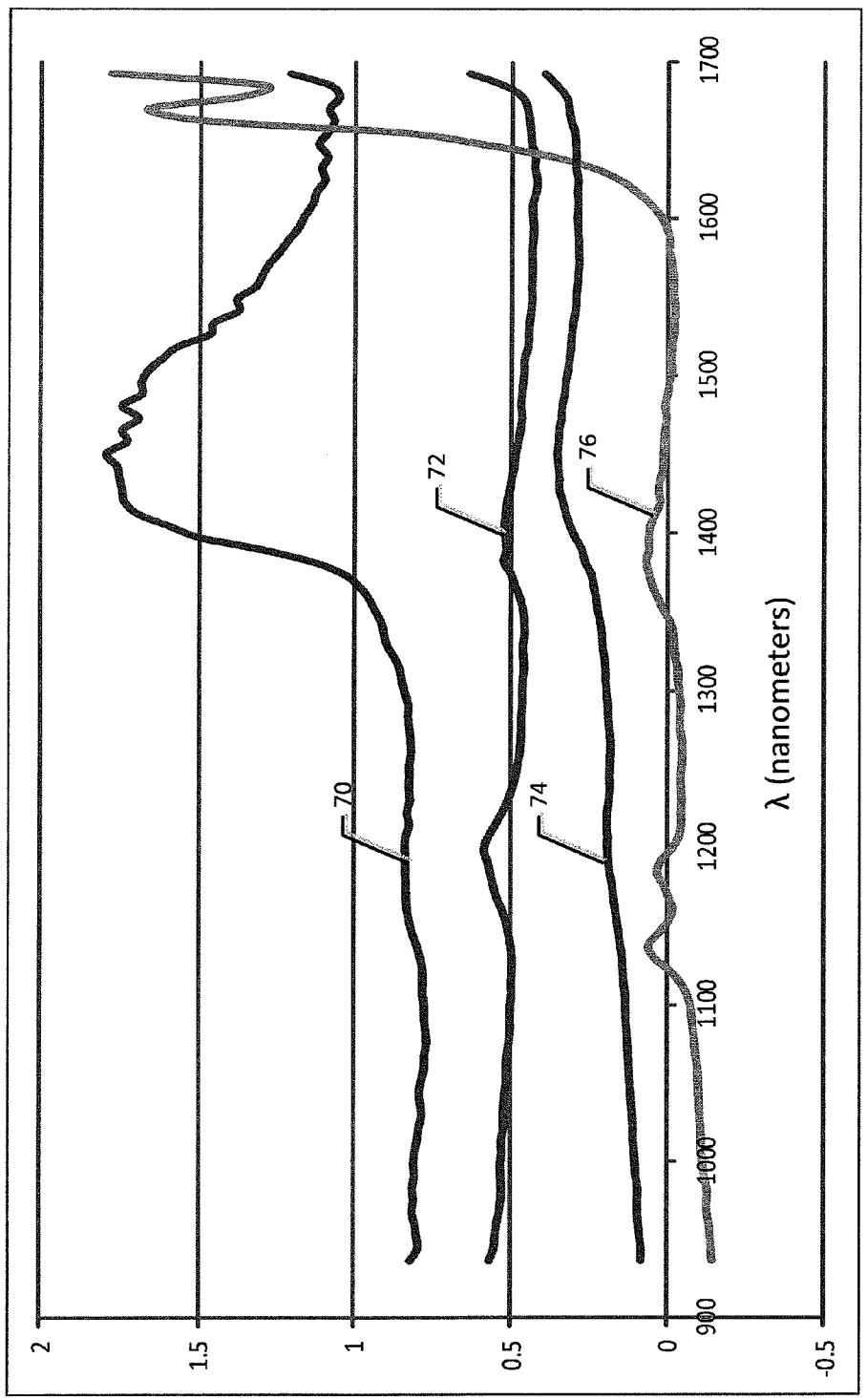

Having thus described aspects of the present disclosure in general terms, reference will now be made to the accompanying drawings, which are not necessarily drawn to scale, and wherein:

FIG. 1 is a plan view of a system for laying up composite material in accordance with an example embodiment of the present disclosure;

FIG. 2 is a block diagram of a system for laying up composite material including a multispectral imaging system in accordance with an example embodiment of the present disclosure;

FIG. 3 is a block diagram of operations performed, such as by the multispectral imaging system of FIG. 2, in accordance with an example embodiment of the present disclosure;

FIG. 4 is a representation of the different spectra of near infrared light that are captured over time at different locations along the composite structure that is being fabricated in accordance with an example embodiment of the present disclosure;

FIG. 5 is a graphical representation of the predefined spectral signatures of several different types of foreign object debris in response to illumination by near infrared light in accordance with an example embodiment of the present disclosure; and FIGS. 6a-6d are example images of different types of foreign object debris following illumination by near infrared light in accordance with an example embodiment of the present disclosure.

DETAILED DESCRIPTION

The present disclosure now will be described more fully hereinafter with reference to the accompanying drawings, in which some, but not all aspects are shown. Indeed, the disclosure may be embodied in many different forms and should not be construed as limited to the aspects set forth herein. Rather, these aspects are provided so that this disclosure will satisfy applicable legal requirements. Like numbers refer to like elements throughout.

A multispectral system and method are provided in accordance with example embodiments of the present disclosure in order to detect foreign object debris upon composite material. The multispectral system and method of an example embodiment illuminate the composite material with near infrared light and, in accordance with some example embodiments, with near infrared light having a wavelength within only a portion of the near infrared spectrum. As a result, the multispectral system and method may detect foreign object debris on the composite material in a timely and efficient manner, thereby permitting foreign object debris to be identified while simultaneously applying another layer of composite material, such as a composite ply, to an underlying workpiece, such as with an automatic fiber placement apparatus. Consequently, the multispectral system and method permit foreign object debris to be identified and addressed in a manner that allows layers of composite material to be applied at a relatively rapid rate, thereby facilitating the fabrication of relatively large composite structures in a timely manner.

The multispectral system and method may be employed in conjunction with the identification of foreign object debris upon composite material during the fabrication of any of a wide variety of composite structures. For example, a composite structure that is fabricated during inspection by the multispectral system and method may be a portion of a vehicle, such as a portion of a space craft, a marine vehicle, an aircraft, e.g., an aircraft wing, a stringer, the skin or the like. However, other types of composite structures may be fabricated during inspection by the multispectral system and method to identify foreign object debris. Additionally, the composite material that is applied during inspection by the multispectral system and method may be any of a variety of composite materials including, for example, carbon and glass fiber based composite materials in which carbon and/or glass fibers are embedded in a resin matrix, e.g., a polymer matrix.

As shown in FIG. 1, a layer 10 of composite material may be applied by an automatic fiber placement apparatus 12. The automatic fiber placement apparatus is configured to move along the surface of a workpiece 14, such as a form or one or more underlying layers of composite material. As the automatic fiber placement apparatus moves along the workpiece, such as from the left to the right as indicated in FIG. 1, the automatic fiber placement apparatus applies a layer of composite material, such as by applying a composite ply to the underlying composite plies. The automatic fiber placement apparatus may urge the most recently applied layer of composite material toward the underlying workpiece, such as by applying a compacting force with a roller 16 or other mechanism for applying a compacting force to the composite ply. The automatic fiber placement apparatus may be configured to move along the workpiece at a predefined speed so as to apply the layer of composite material at a predefined rate, such as 16 inches per second, 23 inches per second, 60 inches per second or more.

During the application of a layer 10 of composite material, the automatic fiber placement apparatus 12 may be initially positioned at a predefined start location and the automatic fiber placement apparatus of an example embodiment may then track the speed and direction at which it moves across the workpiece 14. As such, the automatic fiber placement apparatus of this example embodiment may be configured to determine its current location, either in absolute coordinates, part coordinates or relative coordinates with respect to the start location.

Although the automatic fiber placement apparatus 12 may be preprogrammed so as to move at a predetermined speed and in a predetermined path across the workpiece 14, the automatic fiber placement apparatus of an example embodiment may operate under control of an automatic fiber placement controller 18 as shown, for example, in FIG. 2. In this regard, the automatic fiber placement controller may control the operation of the automatic fiber placement apparatus and may direct the automatic fiber placement apparatus to move across the workpiece at a selectable speed and in a selectable direction while applying the layer 10 of composite material. Thus, the automatic fiber placement controller of this example embodiment may be configured to determine the current location of the automatic fiber placement apparatus.

The automatic fiber placement apparatus 12 is configured to move relative to the workpiece 14. In this regard, the automatic fiber placement apparatus may move across a stationary workpiece. Alternatively, the workpiece may be moved relative to a stationary automatic fiber placement apparatus. Still further, both the automatic fiber placement apparatus and the workpiece may be moved so as to create relative motion therebetween. Regardless, the automatic fiber placement apparatus moves relative to the workpiece so as to apply the layer 10 of composite material to the workpiece.

In addition to the automatic fiber placement apparatus 12, a system for composite layup in accordance with an example embodiment of the present disclosure also includes a multispectral imaging system configured to inspect the workpiece 14. In this regard, at least portions of the multispectral imaging system are configured to move in concert with the automatic fiber placement apparatus relative to the workpiece. As shown in FIG. 1, for example, the multispectral imaging system 20 may be carried by the automatic fiber placement apparatus so as to move therewith across the workpiece. As described in further detail below, the multispectral imaging system is configured to illuminate the surface of the composite material with near infrared light and to detect the near infrared light following interaction of the near infrared light with the composite material, such as by detecting the near infrared light that reflects from the surface of the composite material.

In the embodiment of FIG. 1, the multispectral imaging system 20 is configured to illuminate a portion of the surface of the composite material 14 in advance of the automatic fiber placement apparatus 12 in the direction in which the automatic fiber placement apparatus is moving, such as indicated by dashed line 22. As such, the multispectral imaging system of this example embodiment is configured to inspect the surface of the workpiece 14 prior to the application of the next layer 10 of composite material being overlaid onto the workpiece 14. In an instance in which foreign object debris 24 exists upon the surface of the workpiece 14 that is inspected by the multispectral imaging system, the foreign object debris will alter the near infrared light that returns to the multispectral imaging system. As described below, the multispectral imaging system may therefore detect the presence of foreign object debris and, in some embodiments, may identify the type of foreign object debris. In an instance in which foreign object debris is detected upon the composite material, the multispectral imaging system may cause the relative movement of the automatic fiber placement apparatus to be halted prior to covering the foreign object debris with another layer of composite material. As such, the foreign object debris may be removed or otherwise addressed such that the layer 10 is not overlaid onto the foreign object debris with the foreign object debris then being encapsulated between the layer 10 and the workpiece 14.

Alternatively, the fabrication process may continue unabated by the detection of foreign object debris. However, by identifying the type and the location of the foreign object debris, such as described below, the layers of composite material that overlie foreign object debris may be lifted or otherwise temporarily removed in order to provide access to the foreign object debris and to permit its removal.

The resulting composite structure may therefore have less foreign object debris and, as a result, be of higher quality. Moreover, by detecting the foreign object debris prior to overlaying another layer 10 of composite material thereupon, the foreign object debris may be removed or otherwise addressed in an efficient manner such that the fabrication process proceeds in a more expeditious manner.

Referring now to FIG. 3 which depicts the operations performed by a multispectral imaging system 20 of an example embodiment, the multispectral imaging system is configured to illuminate the surface of the workpiece 14 with near infrared light. See block 50. As shown in FIG. 2, the multispectral imaging system includes a near infrared light source 30. The near infrared light source may be embodied in various manners. For example, the near infrared light source may include one or more near infrared lasers having respective center frequencies within the near infrared spectrum. In an embodiment in which the near infrared light source includes a plurality of near infrared lasers, the near infrared lasers may have different center frequencies, all of which are within the near infrared spectrum. Alternatively, the near infrared light source may be a tungsten halogen light source configured to emit a broad range of light wavelengths within the near infrared spectrum.

Regardless of the type of near infrared light source 30, the near infrared light source of an example embodiment may be configured to illuminate the surface of the composite material 14 with light having a wavelength within only a portion of the near infrared spectrum. In this regard, the near infrared spectrum extends from 750 nanometers to 2500 nanometers. As such, the near infrared light source of an example embodiment is configured to illuminate the surface of the composite material only with light having wavelengths between 900 nanometers and 2500 nanometers. In another embodiment, the near infrared light source is configured to illuminate the surface of the composite material only with light having wavelengths between 900 nanometers and 1700 nanometers.

The near infrared light source 30 may provide broad band illumination across at least a portion of the infrared spectrum, such as between 900 nanometers and 1700 nanometers. Alternatively, the near infrared light source may provide a plurality of discrete near infrared wavelengths, such as the wavelengths that permit different types of foreign object debris to be most reliably identified and distinguished. In this embodiment, the near infrared light source may provide each discrete near infrared wavelength at a respective illumination angle relative to the composite structure with the illumination angle either being the same for all wavelengths or being different for at least some wavelengths so as to enhance the detection of foreign object debris.

By limiting the spectrum of wavelengths with which the near infrared light source 30 illuminates the surface of the composite material 14, the multispectral imaging system 20 and method may collect the requisite data in order to identify various types of foreign object debris, but may do so in a manner that effectively limits the data that is collected and processed, such as to data relating to the spectrum between 900 nanometers and 2500 nanometers and, in one embodiment to the spectrum between 900 nanometers and 1700 nanometers as opposed to collecting and processing data relating to the entire near infrared spectrum. By limiting the data to a portion of the near infrared spectrum, the multispectral imaging system and method of an example embodiment may perform the analysis and identification of foreign object debris 24 more quickly, thereby permitting foreign object debris to be identified quickly which is of import in order to remove or otherwise address the foreign object debris in advance of the application of another layer 10 of composite material by an automatic fiber placement apparatus 12 over the foreign object debris. Specifically, reducing the amount of data collected and analyzed, enables an operational speed of the automatic fiber placement apparatus 12 to be increased, which thus increases the quantity of composite material that can be applied so as to reduce the overall time to fabricate the workpiece 14 while increasing the quality of the final workpiece.

Limiting the spectrum of near infrared light, such as to that having wavelengths between 900 nanometers and 2500 nanometers and, more specifically, between 900 nanometers and 1700 nanometers, not only is the amount of data that is collected and processed correspondingly limited, but the particular spectrum of near infrared wavelengths that is utilized is that which is most responsive to different types of foreign object debris 24. Thus, the spectrum of near infrared wavelengths that is utilized to inspect the underlying layers of composite material 14 permit foreign object debris to be reliably identified and permits the multispectral imaging system 20 and method to distinguish between different types of foreign object debris, thereby maintaining the quality of the detection process while increasing the speed with which a foreign object debris is detected.

As shown in block 52 of FIG. 3, the multispectral imaging system 20 is also configured to detect the near infrared light following interaction with the composite material 14, such as following the reflection of the near infrared light from the composite material and any foreign object debris 24 upon the composite material. As shown in FIG. 2, the multispectral imaging system 20 includes a detector 32 configured to detect the near infrared light returning from the composite material. In an example embodiment, the detector comprises an array of detector elements with each detector element corresponding to a respective pixel in the resulting image created by the near infrared light that is received. Various types of detector elements may be employed, but in example embodiment, the detector includes an array of indium arsenide (InAs) detector elements or an array of indium antimony (InSb) detector elements.

The detector 32 may be configured in various manners. In an example embodiment, the detector includes a linear array of detector elements. For example, in an embodiment in which the automatic fiber placement apparatus 12 is configured to move in a longitudinal direction, the detector may include a linear array of detector elements extending in a lateral direction, perpendicular to the longitudinal direction in which the automatic fiber placement apparatus advances. In addition, the detector may include any number of detector elements, such as a linear array of 320 detector elements in one example embodiment.

In an example embodiment, the detector 32 detects infrared light at each of a plurality of discrete wavelengths, such as the wavelengths that permit different types of foreign object debris to be identified and distinguished. In another embodiment in which the multispectral imaging system 20 is a hyperspectral imaging system, the detector is configured to detect infrared light across a spectrum of infrared wavelengths, such as between 900 nanometers and 2500 nanometers or between 900 nanometers and 1700 nanometers.

In an embodiment in which the automatic fiber placement apparatus 12 advances in a longitudinal direction across the surface of underlying composite material 14, the multispectral imaging system 20 may be configured to repeatedly illuminate the surface of the composite material with near infrared light and to correspondingly repeatedly detect the near infrared light returning following the interaction with the composite material. As a result of the advancement of the automatic fiber placement apparatus and the movement of the near infrared light source 30 and the detector 32 of the multispectral imaging system in concert with the automatic fiber placement apparatus, the repeated illumination and detection of the multispectral imaging system causes different portions of the composite material to be inspected in the direction in which the automatic fiber placement apparatus advances.

As shown in FIG. 4, for example, in an instance in which the automatic fiber placement apparatus 12 advances in a longitudinal direction (designated y) along a workpiece 14, the multispectral imaging system 20 may repeatedly illuminate the surface of the workpiece with near infrared light and detect the returning near infrared light, thereby inspecting different portions of the composite material spaced apart from one another in the y direction. In this regard, FIG. 4 depicts the multispectral imaging system illuminating the surface of the composite material at three different locations as the automatic fiber placement apparatus advances in the y direction as indicated by the fan-shaped representation of the near infrared light at 22a, 22b and 22c. In response to each illumination of the surface of the composite material, the detector 32 of the multispectral imaging system detects the near infrared light returning following its interaction with the composite material, thereby creating three distinct images from the near infrared light that is captured at three different points in time by the detector. FIG. 4 depicts the three images 14a, 14b and 14c that are created in response to illumination of the workpiece with the near infrared light at 22a, 22b and 22c, respectively. The multispectral imaging system and method may be configured to capture any number of images with any desired spacing (in the y direction) therebetween. For example, the multispectral imaging system and method may be configured to capture many more images with much smaller spacing between the images than that depicted in FIG. 4. Additionally, the images 14a, 14b and 14c of FIG. 4 are the product of illumination of the surface of the workpiece with a continuous spectrum near infrared light, such as from 900 nanometers to 1700 nanometers. However, the multispectral imaging system may, instead, illuminate the surface with discrete, non-continuous wavelengths of near infrared light spaced across a range of wavelengths, such as spaced between 900 nanometers and 1700 nanometers, such as in an instance in which the near infrared light source 30 includes a plurality of near infrared lasers with different center frequencies.

In the example embodiment of FIG. 4 in which the detector 32 includes a linear array of detector elements that capture near infrared light that returns following its interaction with a respective portion of the surface of the composite material 14, each image captured by the detector corresponds to a respective location in the y direction from which the near infrared light was reflected. As shown in FIG. 4, each image may span a range in the lateral or x direction as a result of the linear array of detector elements extending in the lateral or x direction. Further, each detector element is configured to capture a spectrum of near infrared light across the range of wavelengths of near infrared light with which the composite material is illuminated. Thus, each detector element is configured to determine the intensity of the near infrared light that was received at each of the different wavelengths of near infrared light with which the surface of the composite structure was illuminated. With reference to the images depicted in FIG. 4, at a respective location in the y direction, the resulting image may be two-dimensional with the x dimension representing each different detector element of the linear array and the z dimension representing the intensity of near infrared light received by the respective detector element at each of the different wavelengths of near infrared light with which the composite material was illuminated. The spacing between the images in the y direction in this example embodiment depends upon the size of foreign object debris that is to be reliably detected. For example, the step size between images in the y direction may be one-half the size of the smallest foreign object debris (in the same y direction) that is to be detected. In an instance in which foreign object debris that is 0.25 inches or larger in size is to be detected, the step size between images in the y direction is 0.125 inches or less.

As shown in block 54 of FIG. 3, the multispectral imaging system 20 is also configured to analyze the spectrum of the near infrared light that is captured by the detector 32 to detect foreign object debris 24 upon the composite material 10. In this regard, the multispectral imaging system includes processing circuitry 34 configured to analyze the spectrum of near infrared light following the detection of the near infrared light returning following its interaction with the surface of the composite material. The processing circuitry may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. In some example embodiments, the processing circuitry is configured to execute instructions stored in memory 36 or otherwise accessible to the processing circuitry. These instructions, when executed by the processing circuitry, may cause one or more of the functionalities described herein to be performed. As such, the processing circuitry and the memory may comprise an entity capable of performing operations according to embodiments of the present disclosure while configured accordingly. Thus, for example, when the processing circuitry is embodied as an ASIC, FPGA or the like, the processing circuitry and the memory may comprise specifically configured hardware for conducting one or more operations described herein. Alternatively, as another example, when the processing circuitry is embodied as an executor of instructions, such as may be stored in the memory, the instructions may specifically configure the processing circuitry to perform one or more algorithms and operations described herein. Regardless of the manner in which the processing circuitry is embodied, the processing circuitry may be configured to rapidly download the images from the detector 32, such as by utilizing a Camera Link protocol.

The memory 36 may include, for example, volatile and/or non-volatile memory. The memory may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory may comprise any non-transitory computer readable storage medium. The memory may be configured to store information, data, applications, instructions, or the like for enabling the processing circuitry 34 to carry out various functions in accordance with example embodiments of the present disclosure. For example, the memory may be configured to store program instructions for execution by the processing circuitry.

The processing circuitry 34 of this example embodiment is configured to analyze the spectrum of near infrared light that is received by the detector 32 by distinguishing between different types of foreign object debris 24. In this regard, the processing circuitry may be configured to compare the spectrum of near infrared light that is received by each detector element of the detector to predefined spectral signatures representative of a plurality of different types of foreign object debris. In this regard, different types of foreign object debris may respond differently to irradiation by near infrared light and, more particularly, to near infrared light having wavelengths between 900 nanometers and 1700 nanometers. As shown in FIG. 5, for example, the predefined spectral signatures of four different types of foreign object debris in response to irradiation by near infrared light having wavelengths between 900 nanometers and 1700 nanometers are depicted. In this regard, spectral signature 70 corresponds to a drop of water, spectral signature 72 corresponds to a rubber band, spectral signature 74 corresponds to chewing gum and spectral signature 76 corresponds to safety glasses. Each spectral signature is unique and distinguishable. The predefined spectral signatures may be stored in a file 38 within memory 36 in an example embodiment. The spectral signatures 70, 72, 74 and 76 of FIG. 4 are the product of illumination of the foreign object debris with a continuous spectrum near infrared light, such as from 900 nanometers to 1700 nanometers. As noted above, however, the multispectral imaging system may, instead, illuminate the foreign object debris with discrete, non-continuous wavelengths of near infrared light spaced across a range of wavelengths, such as spaced between 900 nanometers and 1700 nanometers.

The processing circuitry 34 is therefore configured to compare the spectrum of near infrared light that was received by each detector element of the detector 32 to each of the predefined spectral signatures. In an instance in which the spectrum of near infrared light received by a detector element matches a predefined spectral signature, such as by being identical to a predefined spectral signature or being within a predefined range, such as 5%, 1% or the like, of a predefined spectral signature, the processing circuitry may flag the respective pixel of the near infrared image that corresponds to the detector element as being indicative of the respective type of foreign object debris having the matching spectral signature.

In response to determining that a spectrum of near infrared light received by the detector 32 matches a predefined spectral signature, the processing circuitry 34 may be configured to identify foreign object debris upon the composite material 14 to be of the respective type that has the matching predefined spectral signature. See block 56 of FIG. 3. Since each detector element may correspond to a relatively small region of the composite material, such as a square having dimensions of 0.004 inch×0/004 inch, the processing circuitry of an example embodiment may analyze the results of the comparison of the spectrum of near infrared light received by various detector elements to the predefined spectral signatures for each of a plurality of detector elements and may be configured to identify foreign object debris of a respective type to be upon the composite material only in an instance in which a predefined number of adjacent detector elements, such as four adjacent detector elements, have been identified to have captured a spectrum of near infrared light that matches the same predefined spectral signature. In this instance, the processing circuitry may then identify foreign object debris of a respective type that corresponds to the matching predefined spectral signature to be upon the surface of the composite material. The adjacent detector elements that are considered by the processing circuitry for purposes of identifying foreign object debris may not only be detector elements that are adjacent to one another in the lateral or x direction, but also detector elements that are adjacent in the longitudinal or y direction, thereby representing the output of the same detector element at sequential points in time as the automatic fiber placement apparatus 12 and multispectral imaging system 20 move along the surface of the composite material. The processing circuitry is also configured to determine the size of the foreign object debris based upon the number of adjacent detector elements that capture an image of the foreign object debris.

Figure 6A:
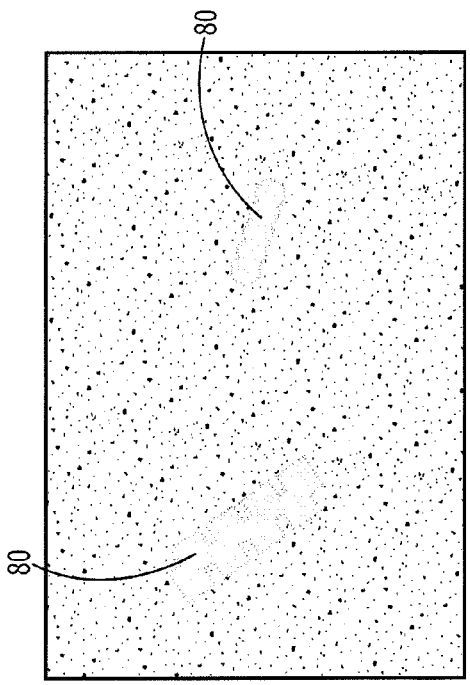
Figure 6B:
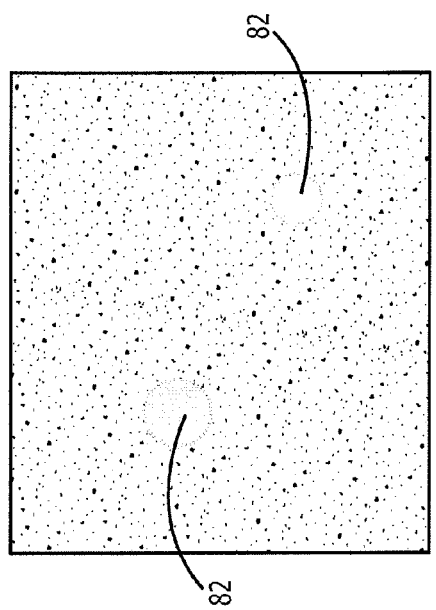
Figure 6C:
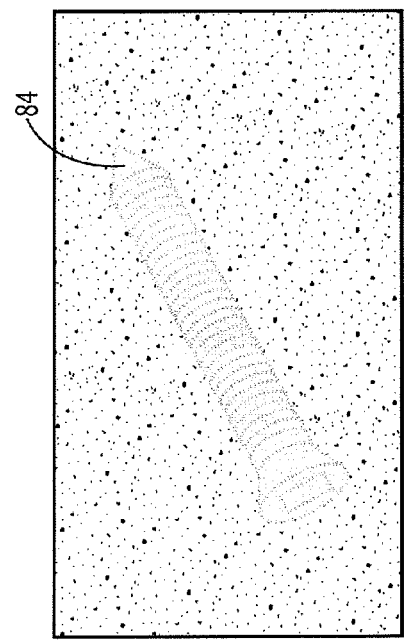
Figure 6D:
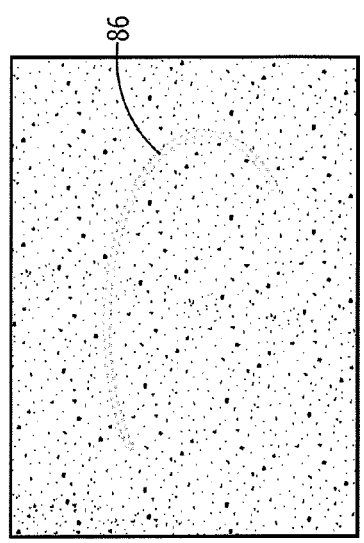

Examples of different types of foreign object debris 24 that may be detected upon the surface of the composite material 14 and the corresponding near infrared images captured by the detector 32 are shown in FIG. 6a-6d. In this regard, FIG. 6a depicts foreign object debris in the form of small plastic parts 80, FIG. 6b depicts foreign object debris in the form of a drop of water 82, FIG. 6c depicts foreign object debris in the form of a socket head screw 84 and FIG. 6d depicts foreign object debris in the form of a piece of wire 86. These types of foreign object debris are provided by way of example and the multispectral imaging system 20 and method may be configured to detect a wide variety of other types of foreign object debris.

As described above, the automatic fiber placement apparatus 12 and/or the automatic fiber placement controller 18 may determine its location during the application of another layer 10 of composite material. As such, the processing circuitry 34 may be in communication with the automatic fiber placement apparatus and/or the automatic fiber placement controller in order to obtain the location, such as in the longitudinal or y direction, of the automatic fiber placement apparatus from which the location at which the surface of the composite material 14 is illuminated may be determined since the surface of the composite material is illuminated at a predefined distance in advance of the automatic fiber placement apparatus. Thus, the processing circuitry may be configured to associate a location with each near infrared image received by the detector 32. Consequently, in an instance in which the processing circuitry identifies foreign object debris upon the surface of the composite material, the processing circuitry may also be configured to identify the location of the foreign object debris upon the composite material based upon the respective location at which the near infrared image was captured. See block 58 of FIG. 3.

The processing circuitry 34 may also be configured to cause a notification to be provided in an instance in which foreign object debris 24 is detected. See block 60 of FIG. 3. For example, the processing circuitry may be configured to cause an image of the foreign object debris, such as a near infrared image of the foreign object debris, to be presented upon a user interface 40 or may otherwise issue a notification via the user interface. As such, an operator may halt the automatic fiber placement apparatus 12 and may determine the manner in which to address the foreign object debris prior to applying another layer 10 of composite material. The manner in which the foreign object debris is addressed may depend upon the type of foreign object debris as determined by the multispectral imaging system 20 and method, as some types of foreign object debris may be more detrimental than other types of foreign object debris. In this regard, the foreign object debris may be removed, such as in an instance in which the operator determines that the type of foreign object debris would adversely impact the resulting composite structure. Alternatively, the foreign object debris may be left in place if the operator determines that the type of foreign object debris will not materially impact the properties of the resulting composite structure. While described above in conjunction with the determination of the manner in which to address the foreign object debris being performed by an operator, the determination may be automated, such as by being performed by the processing circuitry, such that the automatic fiber placement apparatus need not be halted if a determination is made that the type of foreign object debris will not materially impact the properties of the resulting composite structure. Following the removal or otherwise addressing the foreign object debris, the automatic fiber placement apparatus may be restarted so as to continue the automated placement of the composite material. Still further, the fabrication process of an alternative embodiment may continue without pause even if foreign object debris is detected. However, by identifying the type and the location of the foreign object debris, the layers of composite material that overlie foreign object debris may subsequently be lifted or otherwise temporarily removed in order to provide access to the foreign object debris and to permit its removal.

Many modifications and other aspects of the disclosure set forth herein will come to mind to one skilled in the art to which this disclosure pertains having the benefit of the teachings presented in the foregoing descriptions and the associated drawings. For example, although described above in conjunction with an automatic fiber placement apparatus 12 that applies layers 10 of composite material to an underlying workpiece 14, the multispectral imaging system 20 and method may additionally or alternatively inspect composite structures fabricated in other manners. In this regard, the multispectral imaging system and method may be configured to inspect composite structures, such as stringers, formed of discrete pieces of composite preimpregnated material that are applied and then compacted sequentially. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method comprising:
    illuminating a surface of a composite material with near infrared light;
    detecting the near infrared light following interaction of the near infrared light with the composite material; and
    following detection, analyzing a spectrum of the near infrared light to detect foreign object debris upon the composite material, wherein analyzing the spectrum of near infrared light comprises distinguishing between different types of foreign object debris by comparing the spectrum of near infrared light to predefined spectral signatures of the plurality of different types of foreign object debris,
    wherein the illuminating, detecting and analyzing are performed simultaneous with layup of the composite material.

2. A method according to claim 1 wherein detecting the near infrared light comprises separately capturing the spectrum of near infrared light with each of a plurality of detector elements following the interaction of the near infrared light with a respective portion of the composite material, each detector element corresponding to a respective pixel.

3. A method according to claim 2 further comprising identifying foreign object debris of a respective type upon the composite material in an instance in which at least a predetermined number of adjacent pixels have a spectrum of near infrared light that corresponds to the predefined spectral signature of the respective type of foreign object debris.

4. A method according to claim 1 wherein illuminating the surface of the composite material comprises illuminating the surface of the composite material with light having a wavelength within only a portion of the near infrared spectrum.

5. A method according to claim 4 wherein illuminating the surface of the composite material further comprises illuminating the surface of the composite material with light having wavelengths between 900 nanometers and 2500 nanometers.

6. A method according to claim 4 wherein illuminating the surface of the composite material further comprises illuminating the surface of the composite material with light having wavelengths between 900 nanometers and 1700 nanometers.

7. A multispectral imaging system comprising:
    a near infrared light source configured to illuminate a surface of a composite material with near infrared light;
    a detector configured to detect the near infrared light following interaction of the near infrared light with the composite material; and
    processing circuitry, responsive to the detector, configured to analyze a spectrum of the near infrared light to detect foreign object debris upon the composite material, wherein the processing circuitry is configured to analyze the spectrum of near infrared light by distinguishing between different types of foreign object debris as a result of comparing the spectrum of near infrared light to predefined spectral signatures of the plurality of different types of foreign object debris,
    wherein the near infrared light source is configured to illuminate, the detector is configured to detect and the processing circuitry is configured to analyze simultaneous with layup of the composite material.

8. A multispectral imaging system according to claim 7 wherein the detector comprises a plurality of detector elements that are each configured to separately capture the spectrum of near infrared light following the interaction of the near infrared light with a respective portion of the composite material, each detector element corresponding to a respective pixel.

9. A multispectral imaging system according to claim 8 wherein the processing circuitry is further configured to identify foreign object debris of a respective type upon the composite material in an instance in which at least a predetermined number of adjacent pixels have a spectrum of near infrared light that corresponds to the predefined spectral signature of the respective type of foreign object debris.

10. A multispectral imaging system according to claim 7 wherein the near infrared light source is configured to illuminate the surface of the composite material with light having a wavelength within only a portion of the near infrared spectrum.

11. A multispectral imaging system according to claim 10 wherein the near infrared light source is configured to illuminate the surface of the composite material with light having wavelengths between 900 nanometers and 2500 nanometers.

12. A multispectral imaging system according to claim 10 wherein the near infrared light source is configured to illuminate the surface of the composite material with light having wavelengths between 900 nanometers and 1700 nanometers.

13. A system for composite layup, the system comprising:
an automatic fiber placement apparatus configured to apply composite material to a workpiece, wherein the automatic fiber placement apparatus is configured to move relative to the workpiece; and
a multispectral imaging system comprising: a near infrared light source configured to illuminate a surface of the composite material with near infrared light, a detector configured to detect the near infrared light following interaction of the near infrared light with the composite material, and processing circuitry, responsive to the detector, configured to analyze a spectrum of the near infrared light to detect foreign object debris upon the composite material while composite material is applied to the workpiece,
wherein the near infrared light source and the detector are configured to move with the automatic fiber placement apparatus relative to the workpiece while composite material is applied to the workpiece.

14. A system according to claim 13 wherein the processing circuitry is further configured to analyze the spectrum of near infrared light by distinguishing between different types of foreign object debris as a result of comparing the spectrum of near infrared light to predefined spectral signatures of the plurality of different types of foreign object debris.

15. A system according to claim 14 wherein the detector comprises a plurality of detector elements that are each configured to separately capture the spectrum of near infrared light following the interaction of the near infrared light with a respective portion of the composite material, each detector element corresponding to a respective pixel.

16. A system according to claim 15 wherein the processing circuitry is further configured to identify foreign object debris of a respective type upon the composite material in an instance in which at least a predetermined number of adjacent pixels have a spectrum of near infrared light that corresponds to the predefined spectral signature of the respective type of foreign object debris.

17. A system according to claim 13 wherein the near infrared light source is configured to illuminate the surface of the composite material with light having wavelengths only between 900 nanometers and 1700 nanometers.

18. A system according to claim 13 wherein the processing circuitry is further configured to associate a location with foreign object debris detected upon the composite material based upon location information provided by the automatic fiber placement apparatus.

19. A system according to claim 13 wherein the processing circuitry is further configured to cause a notification to be provided of the foreign object debris detected upon the composite material prior to covering the foreign object debris with additional composite material applied by the automatic fiber placement apparatus.

* * * * *